(12) United States Patent
Diasti et al.

(10) Patent No.: US 6,224,375 B1
(45) Date of Patent: May 1, 2001

(54) METHOD OF FABRICATING NEW DENTAL PROSTHESES USING A PATIENT'S EXISTING DENTAL PROSTHESES

(76) Inventors: Adam Diasti; Graham K. Philip, Jr., both of 2502 N. Rocky Point Dr. Suite 1000, Tampa, FL (US) 33607

( * ) Notice: Subject to any disclaimer, the term of this patent is extended or adjusted under 35 U.S.C. 154(b) by 0 days.

(21) Appl. No.: 09/256,455

(22) Filed: Feb. 23, 1999

(51) Int. Cl.$^7$ .................................................. A61C 13/00
(52) U.S. Cl. ............................ 433/213; 264/18; 433/167
(58) Field of Search .............................. 433/213, 49, 214, 433/167; 264/17, 18

(56) References Cited

U.S. PATENT DOCUMENTS

| | | |
|---|---|---|
| 1,899,521 | 2/1933 | Nudell . |
| 2,682,084 * | 6/1954 | Anchors . |
| 3,217,067 * | 11/1965 | Tencate . |
| 3,251,910 | 5/1966 | Barnhart . |
| 3,431,330 | 3/1969 | Cornwell . |
| 4,024,637 | 5/1977 | Colpitts . |
| 4,195,047 * | 3/1980 | Drennan .................................. 264/17 |
| 4,403,961 * | 9/1983 | Gurney .................................... 433/213 |
| 4,431,420 | 2/1984 | Adair . |
| 4,470,815 | 9/1984 | Hazar . |
| 4,500,291 | 2/1985 | Davis et al. . |
| 4,521,193 | 6/1985 | Cialone . |
| 4,681,543 | 7/1987 | Monroy . |
| 4,865,546 * | 9/1989 | Naylor ................................... 433/213 |
| 4,971,735 * | 11/1990 | Uebayashi .............................. 264/17 |
| 5,201,657 | 4/1993 | Koukos . |
| 5,304,063 | 4/1994 | Ginsburg . |
| 5,403,186 | 4/1995 | Ginsburg . |
| 5,607,628 * | 3/1997 | Palazzolo .............................. 264/18 |
| 5,711,668 | 1/1998 | Huestis . |

* cited by examiner

Primary Examiner—Ralph A. Lewis
(74) Attorney, Agent, or Firm—Shlesinger, Arkwright & Garvey LLP

(57) ABSTRACT

In summary, the invention is directed to a method of making a new dental prosthesis from an existing dental prosthesis, including the steps of making a sacrificial positive or pattern of the existing dental prosthesis, and using the sacrificial pattern of the existing dental prosthesis to form a new dental prosthesis. The inventive method likewise includes making a sacrificial pattern of at least a part of an existing denture. The invention further includes the construction of new dentures from a patient's worn dentures, by providing copy or modified copy of the worn dentures into which one can set and arrange the denture teeth. The invention still further includes a dental prosthetic, such as a denture, made by such methods.

37 Claims, 5 Drawing Sheets

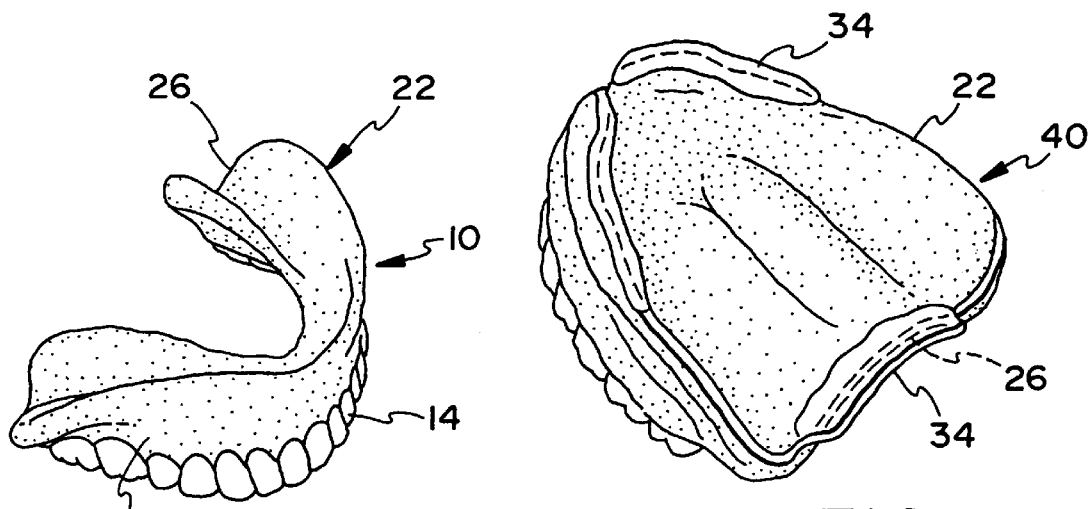
FIG. 1
FIG. 2
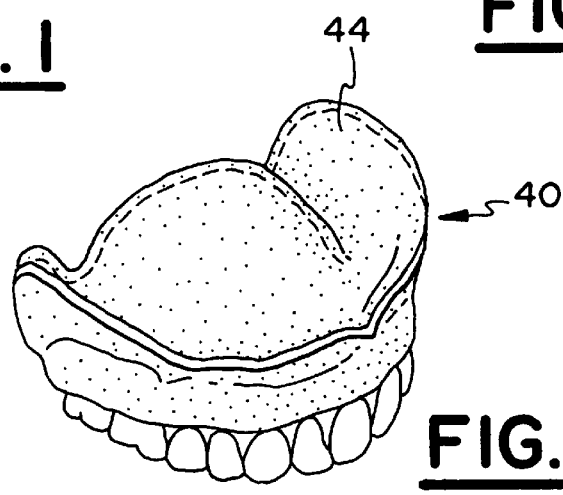
FIG. 3
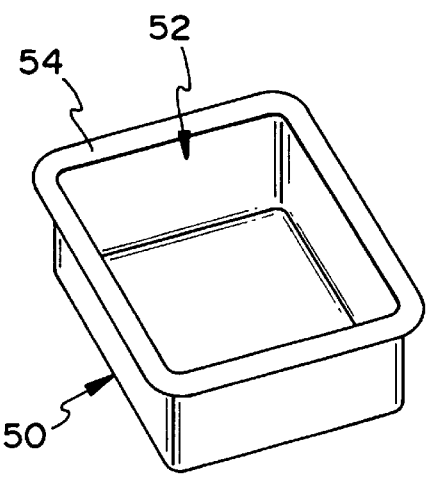
FIG. 4
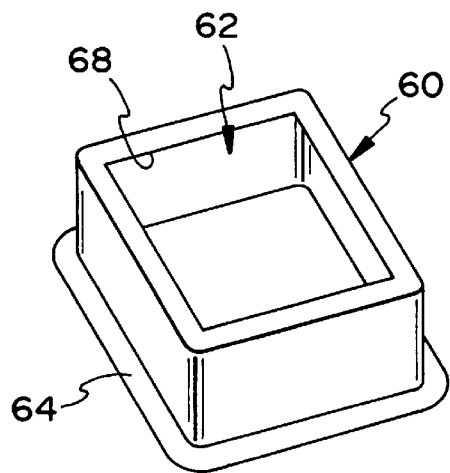
FIG. 5

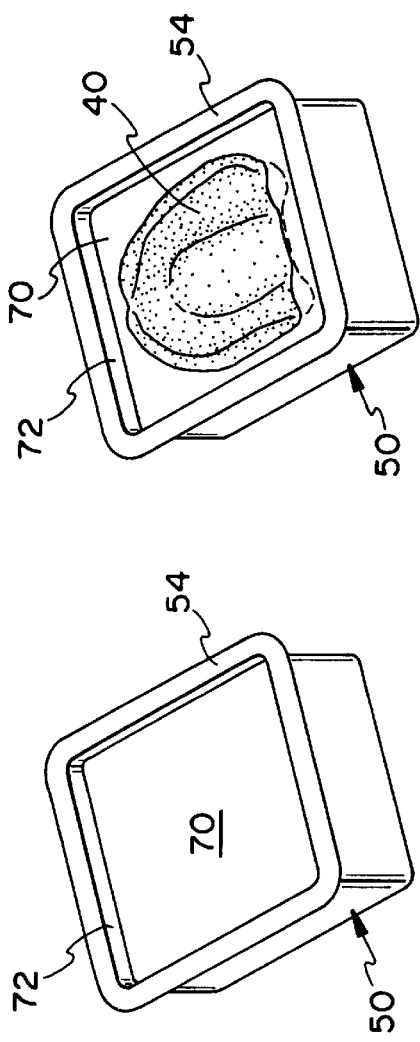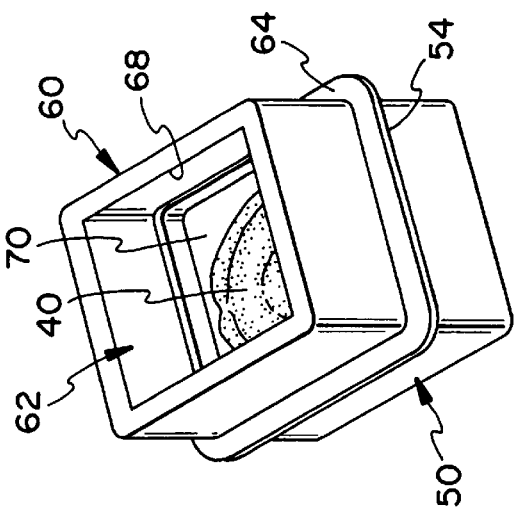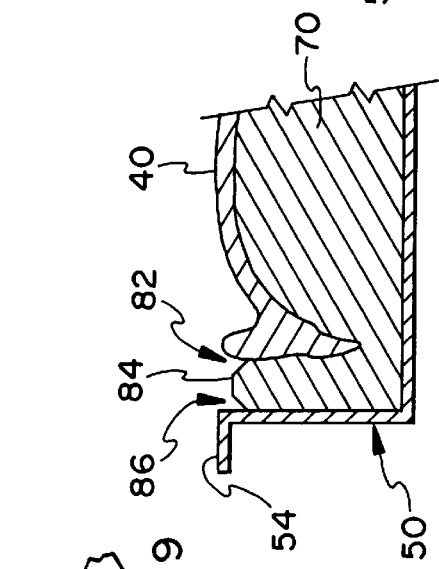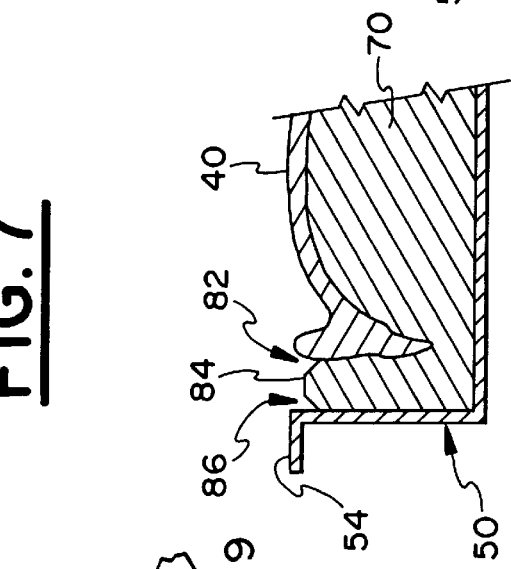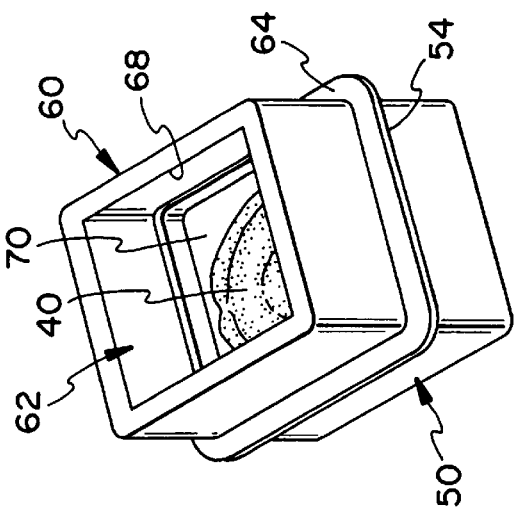

METHOD OF FABRICATING NEW DENTAL PROSTHESES USING A PATIENT'S EXISTING DENTAL PROSTHESES

FIELD OF THE INVENTION

This invention relates to a method of making dental prostheses, and prosthetics made thereby. More specifically, the invention relates to a method of making dentures and dentures made by such methods. Most specifically, the invention relates to a method of making a new denture by making a copy of an existing denture and modifying that copy, as necessary, to make a new denture.

BACKGROUND OF THE INVENTION

Various forms of dental prosthetics, such as so-called "false teeth" have been around of hundreds of years. Many American school children learn that President George Washington wore 18th century dentures which were often ill fitting and which are displayed today at his Mount Vernon home in Alexandria, Va.

Twentieth century examples of dental prosthetics, such as dentures and individual prosthetic teeth are known from the following United States Patents:

U.S. Pat. No. 5,201,657 to Koukos
U.S. Pat. No. 4,500,291 to Davis et al.
U.S. Pat. No. 1,899,521 to Nudell
U.S. Pat. No. 3,251,910 to Barnhart
U.S. Pat. No. 3,431,330 to Cornell
U.S. Pat. No. 4,024,637 to Colpitts
U.S. Pat. No. 4,431,420 to Adair
U.S. Pat. No. 4,470,815 to Hazar
U.S. Pat. No. 4,681,543 to Monroy
U.S. Pat. No. 4,521,193 to Cialone
U.S. Pat. No. 5,304,063 to Ginsburg
U.S. Pat. No. 5,403,186 to Ginsburg
U.S. Pat. No. 5,711,668 to Huestis However, even the most recent known methods of forming dental prostheses and dentures manufactured thereby have significant drawbacks.

Such drawbacks include, in the case of dentures, for example, that a patient must return as many as six (6) to eight (8) times for follow-up appointments in order to have the dentist reshape and reconfigure the denture so that it seats properly in the patient's mouth and feels correct to the patient. Thus, not only are such dentures poor replacements for the patient's existing worn ("old") dentures which must be replaced, but such replacement ("new") dentures often do not feel "right" to the patient.

The multiple return visits to the dentist office are not only annoying to the paying customer, the patient, but also cost the dentist time and money, reduce patient confidence in the dentist, and, occasionally, one losses the patient's patronage.

Other drawbacks of improperly fitting dentures, for example, include patient discomfort, patient dissatisfaction, improperly fitting dentures which tend to move in the patient's mouth and become dislodged, thus impairing the patient's speech and necessitating the use of denture adhesives to compensate for the poor fit, and even a refusal of the patient to wear the ill-fitting dentures.

OBJECTS AND SUMMARY OF THE INVENTION

It is therefore an object of the invention to overcome the drawbacks of the prior art methods and devices.

Another object of the invention is to improve the accuracy and fit of dental prosthetics A further object of the invention is to fabricate new dental prosthetics based on existing or worn dental prosthetics.

A still further object of the invention is to produce modified and corrected new dental prosthetics based on existing or worn dental prosthetics.

A still further object of the invention is to reduce the amount of time required for fabricating new dental prosthetics.

A related object of the invention is to reduce the amount of "chair time" for patients in a dentist's office, for reducing the time required of the patient as well as of the dentist.

Yet another object of the invention is to fabricate dental prosthetics, such as dentures, in two (2) visits to a dentist's office, as opposed to the six (6) or more visits often required by prior art methods.

Yet another object of the invention is to eliminate mounting of models of the dentures on an articulator, for example, in the dentist's office, so that such mounting can be performed more accurately in a laboratory.

A further object of the invention is to eliminate errors which arise during the articulation of models of dental prosthetics, such as often arise during the so-called "pour and mount" method of making dentures.

A yet still further object of the invention is to provide a method of making dental prosthetics which allows the doctor to check and/or implement any corrections to the new dental prosthetics to be made during a patient's first visits to the dentist's office.

Another object of the invention is to provide for a method and dental prosthetic made thereby which allow the technicians associated with the method to have a visual image of the existing denture (as modified/corrected) so that a better dental prosthetic can be made than could be made by prior art methods.

A further object of the invention is to provide for a method of making dental prosthetics which eliminates the requirement for written and numerical information as a guide to construction of a new dental prosthetic, such as written placement information pertaining to the locations of pre-cast prosthetic teeth on the new denture.

Another object of the invention is to minimize the amount of time a patient must wait between his or her initial office visit and the delivery of a completed dental prosthetic, such as a denture.

A yet still further object of the invention is to eliminate the possibility of errors in the new dental prosthetic because of a lack of skills by a dental assistant.

Another object of the invention is to transfer desirable data from the patient's mouth and jaw and/or from an existing dental prosthetic, such as a worn denture to a new denture so that a proper fit and a desirable "feel" is achieved for the patient, while modifying/correcting any undesirable aspects of the existing denture as determined by the dentist.

Another object of the invention is to slow the resorption of bone in the patient's mouth by providing a denture which fits better (e.g., more accurately) than known dentures.

Yet another object of the invention is to eliminate the prior art technique of using gauges to measure the location of teeth to yield a list of numbers by which a lab technician would place prosthetic teeth in a new denture.

A further object of the invention is to eliminate the possibility that an existing dental prosthetic, such as a denture, is broken during the process of using the existing denture as a basis for making a new denture.

Yet another object of the invention is to make a copy of an existing denture during a first office visits so that such copy can be placed in the patient's mouth for an initial fitting during the first office visit.

A still further object of the invention is to modify a copy of the existing denture on a first office visit, such as by placement of a copy of the existing denture in the patient's mouth during the first office visit.

Yet another object of the invention is to provide a method of making a copy of an existing denture during a first office visit that may be shipped to a central location, such as a lab, for conversion into a new denture.

Another object of the invention is to provide a method of making dental prosthetics which avoids fluid pour resin methods which have been known to cause allergic reactions in some patients.

Another object of the invention is to embody all the patient's physical "records" (i.e., the required data such as vertical location, the bite, the position of the teeth) in a physical model as opposed to written records.

Another object of the invention is to provide a method of producing dental prosthetics, such as dentures, which may be used for providing complete upper and lower dentures simultaneously, providing upper dentures alone for patients having natural lower teeth, as well as providing partial dentures.

A yet still further object of the invention is to reduce the number of technicians required to produce dental prosthetics.

Another object of the invention is to reduce the dentist's apprehension associated with shipping off prior art written specifications (i.e., a prescription for a new denture) without having had an opportunity to give the patient a physical fitting ("try-in") of the model of the new dentures prior to shipping the new denture specifications to an outside laboratory.

Another object of the invention is to reduce the length of time required for patients to adapt to new dental prosthetics, such as dentures.

In summary, the invention is directed to a method of making a new dental prosthesis from an existing dental prosthesis, including the steps of making a sacrificial positive or pattern of the existing dental prosthesis, and using the sacrificial pattern of the existing dental prosthesis to form a new dental prosthesis.

The inventive method likewise includes making a sacrificial pattern of at least a part of an existing denture.

The invention further includes the construction of new dentures from a patient's worn dentures, by providing copy or modified copy of the worn dentures into which one can set and arrange the denture teeth.

The invention still further includes a dental prosthetic, such as a denture, made by such methods.

By considering the following detailed description, it will be appreciated that the above objects, as well as others, have been achieved in accordance with the inventive method and inventive apparatus described in detail below.

Throughout the description, relative terms such as upper and lower, left and right are for convenience only and are not intended to be limiting. The term dental prosthetic is intended to include any and all dental prostheses, and the term denture is to intended to include at least partial dentures, as well as entire sets of upper (i.e., maxillary) and lower (i.e., mandibular or lingual) dentures. The term existing or old or worn denture refers to a patient's current denture which requires replacement.

BRIEF DESCRIPTION OF THE DRAWINGS

FIG. 1 illustrates the patient's existing lower or mandibular denture which requires replacement at the time of performing the inventive method; the illustrated existing denture may be a prior art denture or a future denture made according to the inventive method which will require replacement still further in the future;

FIG. 2 illustrates the patient's existing upper or maxillary denture which is to be replaced in accordance with the inventive method; as with the lower denture of FIG. 1, the denture to be replaced may be a prior art denture or a future denture made according to the invention which will need to be replaced still further in the future;

FIG. 3 is another view of the patient's existing upper denture shown in FIG. 2;

FIG. 4 shows the bottom half of the form or box according to the invention in which a part of the method will be carried out;

FIG. 5 illustrates the top half of the form or box according to the invention in which a part of the inventive method according to the invention will be performed;

FIG. 6 illustrates the step of filling the bottom half of the box with a hydrocolloid or other moldable material prior to the step of placing an existing denture therein;

FIG. 7 illustrates the step of placing the existing denture in the hydrocolloid material illustrated in FIG. 6;

FIG. 8 illustrates the step of removing excess set hydrocolloid material adjacent the denture placed therein in FIG. 7;

FIG. 9 is a partial cross sectional view of the inventive step of FIG. 8;

FIG. 10 illustrates the step of placing the mating top of the inventive box on the bottom half of the box after performing the step shown in FIG. 8;

DETAILED DESCRIPTION OF THE INVENTION

Figure 11:
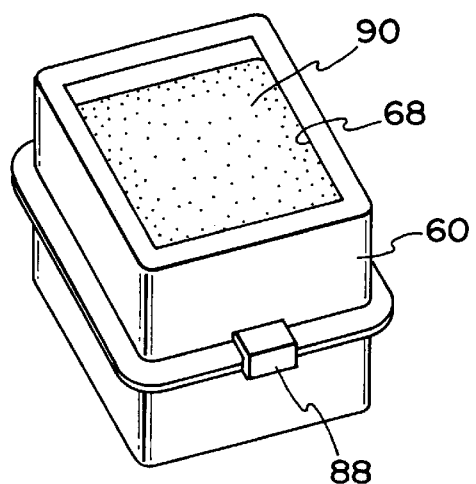
FIG. 11 illustrates the step of clamping the top and bottom halves of the inventive box together and filling the upper regions of the inventive box with a material such as dental stone.

FIG. 1 shows an existing or old or worn patient's denture 10 which is to be replaced with a new denture according to the invention.

Denture 10 is a lower or mandibular denture having synthetic mandibular teeth 14. A buccal flange 18 extends between teeth 14 and a border 22.

Border 22 includes a posterior border 26.

Prior to making a new denture based on existing denture 10, it is preferred that regions of existing denture 10 be modified to provide an enhanced replacement denture.

It is recommended that a new denture be made if the existing denture 10 is more than five (5) years old. In cases with four (4) or less teeth per arch, and immediate package is recommended (i.e., one set then a reline within six (6) months. In multiple extraction cases having five (5) or more teeth per arch, the surgical package (i.e., two (2) sets of dentures) is recommended.

For example, as shown in FIG 2, the edges or borders 22 may be extended by the addition of a suitable material, such as polyvinylsiloxane or suitable waxes 34, e.g., Adaptol (Kaye Research Laboratories of Ashaway, R.I. 02804). By extending the posterior border 26 of an upper or maxillary denture 40 a better replacement denture having such an extended posterior border will result, as will be appreciated from the description below. Such a lengthened posterior border 26 is better owing to there being a greater surface area of denture 10 in the regions were denture 10 adheres to the user's mouth.

As required, the dentist covers any tuberosities in the patient's mouth, extends the posterior dam and/or retromolar pad and buccal shelf, if necessary. Using an indelible pencil, such as a Thompson stick to mark the vibrating line in the mouth prior to making the impression or after the impression is made.

An impression material, such as polyvinylsiloxane, or a rubber base, or a polyether is mixed (as necessary) and then loaded into the existing denture to be copied, such as upper denture 40 of FIGS. 2 and 3 after the borders 26, for example, have been extended. Adhesive is applied to the tissue side of upper denture 40, as required, prior to loading.

One can consider that existing denture 40 is being used as a custom tray.

The loaded existing denture 40 is then placed in the patient's mouth. A suitable amount of impression material is loaded into the upper and lower denture so as to avoid displacement thereof; typically, the minimum amount of impression material is the suitable amount. This procedure often opens the so-called vertical by about 3–4 mm, which opening often is a suitable amount to compensate for the vertical loss owing to resorption of bone under the patient's ridge and natural wear of the denture teeth. By making a new denture, such resorption is slowed owing to the provision of a correctly fitting new denture. The patient's mouth may be chilled with a cold wash to shrink the mouth tissue. The cold was and an impression material wash may add 2–4 mm to the height of the new denture. That height compensates for the bone resorption as well as compensates for the wear on the synthetic teeth of the existing denture 40.

The impression material typically sets in 4–5 minutes.

FIG. 3 illustrates existing upper denture 40 after impression material 44 has set, and upper denture 40 has been removed from the patient's mouth.

The dentist checks the impressions made in the impression material 44 by the patient's mouth; i.e., by the tissue or jaw side of the patient's mouth.

Typically, the above steps may be performed by the dentist.

The following steps of duplicating the now corrected old denture 40 may be carried out by a dental assistant or laboratory ("lab") technician, for example.

The technician may be heating up any material such as a dental wax or making preparations for use of a dental acrylic, for example, which will be used as the sacrificial material of the positive or pattern of the new denture to be made. When using acrylic or any resilient material which will be used for the sacrificial material, any and all undercuts should be blocked out with a non-resilient material (such as a wax) to avoid harming the stone cast.

FIGS. 4 and 5 illustrate, respectively, the bottom and the top halves of the box or form in which many steps of the process are carried out.

Specifically FIG. 4 illustrates a lower box 50 having an open interior or cavity 52 an outwardly extending flange 54.

FIG. 5 illustrates the top half or upper box 60 which likewise has an interior or cavity 62 and a flange 64. A hole 68 which opens to interior 62 is provided on the side of box 60 opposite to flange 64.

While the sacrificial material, such as wax, is being prepared such as by heating, the dental assistant may be preparing a first material 70, such as a hydrocolloid in which existing upper denture 40 will be placed for making a negative mold thereof. Good results have been achieved when an irreversible hydrocolloid, such as Alginate (Henry Schein of Germany) is used. It is also contemplated that reversible hydrocolloids, and the like be used. It is likewise contemplated that other silicone impression materials may be used.

In the case where the assistant uses a hydrocolloid which is supplied in a powdered form, the assistant measures out a suitable amount of the hydrocolloid into a container, and adds the required amount of water. After the hydrocolloid has been adequately mixed, hydrocolloid 70 is poured into lower box 50, as shown in FIG. 6. It does not matter if the mixed hydrocolloid 70 is lumpy or has bubbles therein. It is noted that hydrocolloid 70 such as Alginate, is typically used in the patient's mouth, and not on the patient's dentures, although the mixture will typically be thinner when used with the patient's dentures than when used in the patient's mouth.

Preferable, hydrocolloid 70 is filled up to a level below flange 54 at a distance 72 below the flange. In that manner there will be adequate room for displacement of the hydrocolloid 70 when upper denture 40 is placed therein. That is, there will be adequate room for the level of hydrocolloid 70 to rise without hydrocolloid 70 flowing onto and/or over flange 54. Still further, good results have been achieved when the distance 72 is sufficiently great so that even after denture 40 has been placed into hydrocolloid 70 and the upper level of hydrocolloid 70 has risen, there will still be a space between the surface of hydrocolloid 70 and flange 54. The benefit of having such a free volume is that such volume will eventually be occupied by dental stone and will serve useful purposes, as will be appreciated from the description below.

The assistant places denture 40 in hydrocolloid 70.

FIG. 7 illustrates upper or maxillary denture 70 disposed in hydrocolloid 70. Preferably, the free edges of border 22 of upper denture 40 extend above the top surface of hydrocolloid 70 in the case where denture 40 is an adult human denture. In the case of human dentures, the upper free edge or periphery of the dentures should extend above the upper surface of the hydrocolloid by about 1–2 mm.

The assistant may tap on denture 40 to assist in the placement of the free edges of borders 22 within 1–2 mm of the free surface of hydrocolloid 70, as desired.

Hydrocolloid 70 typically sets in 2–3 minutes, depending on the amount of water added to the typical powdered hydrocolloid.

FIG. 8 illustrates denture 40 disposed in hardened/set hydrocolloid 70. After hydrocolloid 70 has set, the assistant may trim away hardened hydrocolloid from the periphery or borders 22 of denture 40. Namely, the assistant makes removed portions 32, such as by cutting away hydrocolloid 70 along an angled face 84. Removed portion 82 assists in the separation and removal of hardened dental stone in a later part of the inventive method, as will be discussed in detail below.

If hydrocolloid 70 has flowed up to the edge of flange 54, or near thereto, one should likewise trim down hydrocolloid 70 in that region. For example, one should form one or more removed regions 86 adjacent the wall of box 50, such as by cutting away hydrocolloid 70 in that region. Regions 86 may be made at least at one or more of the corners of box 50.

One should be conservative in trimming the borders of the denture so that 1–2 mm of all the borders are exposed. All the alginate must be removed from the impressed surfaces; i.e., from the tissue side of the dentures, especially the posterior border of the maxillary denture, and the retromolar pad area of the mandibular denture.

The assistant then places upper box 60 upside down on lower box 50 so that respective flanges 64 and 54 mate.

One or more clips 88 may be used to secure box 60 to 50.

FIG. 11 illustrates how the assistant then fills upper box 60 with a dental stone or other suitable plaster-like material 90 poured through opening 68. As will be appreciated, not only is interior or cavity 62 of upper box 60 filled with dental stone 90, but also the various open voids which receive dental stone 90 therein, such as, most importantly, the negative of the patient's jaw and flesh portions defined by molded impression material 44, removed portion 82, and the removed regions 86 adjacent box 50, Dental stone 90 may be poured in small increments, with one occasionally tapping the box against a hard surface to allow air bubbles to come to the surface of dental stone 90. It does not matter if some of dental stone 90 seeps out of the sides of the boxes 50 and 60. Typically, one would want to add sufficient dental stone 90 so as to create approximately a 0.5 inch base for the hardened stone model which will be eventually mounted on an articulator 180, as will be described below.

To hasten hardening of dental stone 90, the assistant may mix the powered dental stone up with so-called slurry water, instead of tap water, for example. The mixed, unhardened dental stone 90 will have a thick flowing consistency.

After dental stone 90 has hardened, clips 88 are removed and upper box 60 is detached from lower box 50.

Denture 40 often remains on hardened dental stone 90 in upper box 60 when upper box 60 has been detached from lower box 50. Denture 40 typically releases from hardened hydrocolloid 70 disposed in bottom box 60. Thus, the dentist carefully removes denture 40 from dental stone 90, which removal is generally easily carried out. Thanks to the ready releasing of denture 40 from dental stone 90, denture 40 is rarely cracked or broken.

It will now be seen that one has cast a dental stone negative 92 of the jaw side of denture 40.

Regions of the dental stone negative 92 of the jaw side of denture 40 that corresponds to border 22 of denture 40 are designated as grooves 94.

Prior to the step of adding wax to regions of dental stone negative 92 of the jaw side of denture 40, such as filling grooves 94 with wax (FIG. 15 described in detail below) a sprayer 96 may be used to spray an oil or other lubricant 98 onto the exposed surfaces of hardened dental stone 90; i.e., on dental stone negative 92 and on a land portion 100. Such spray oils may include laboratory lubricants, home cooking oil aerosol sprays, and the like. Alternatively, good results have been achieved by spreading a layer of petroleum jelly on the exposed surfaces of stone 90 with a brush. Typically, a thin layer of petroleum jelly is carefully applied, so that no excess petroleum jelly is present that will interfere with the later steps.

Figure 13:
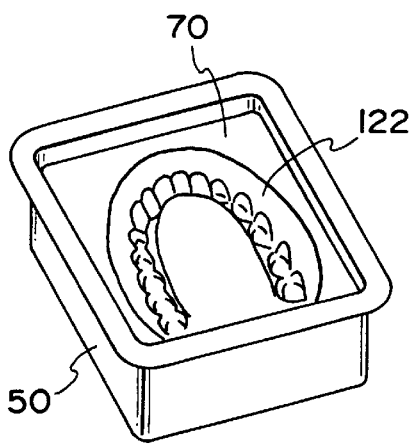
FIG. 13 illustrates the bottom half of the inventive box after the setting of the dental stone poured in the step of FIG. 11, after the top and bottom halves of the box have been separated, and illustrating the hydrocolloid negative of the teeth and flanges of the existing denture after the existing denture has been removed from the set hydrocolloid.

FIG. 13 illustrates the bottom box 50 after separated from top box 60 following the hardening of dental stone 90, as shown in FIG. 11. FIG. 13 specifically shows the hardened hydrocolloid 70 from which the lingual side of denture 40 has been removed after the bottom box 50 and upper box 60 have been separated following the hardening of dental stone 90 of FIG. 11. Thus, FIG. 13 illustrates a hydrocolloid negative 102 of the lingual portion of denture 40; i.e., the tooth and gum portion of denture 40 which faces the patient's tongue.

Typically, denture 40 can be readily separated from hardened hydrocolloid 70; i.e., from hydrocolloid negative 102.

Typically one will now return the existing denture 40 to the patient after a dental stone negative 92 and hydrocolloid negative 102 have been successfully formed. As assistant will generally clean and disinfect denture 40 and return such to the patient, requesting the patient to wait in the waiting area or to return to the dentist office in about half an hour for the try-in part of the procedure involving checking of the fit of a wax positive copy of the entire denture, as will be described in detail below.

By pouring dental stone 90 onto the hydrocolloid 70, past prior art problems of stone protrusions on the stone cast that had to be ground down in order to gain ready access to the borders of the patient's existing denture 40 in order to remove such have been eliminated; such also prevents the locking in of existing denture 40 by the cast stone 90, which locking in had led to breaking of denture 40 using prior art techniques when attempting to dislodge locked in denture 40.

Figure 14:
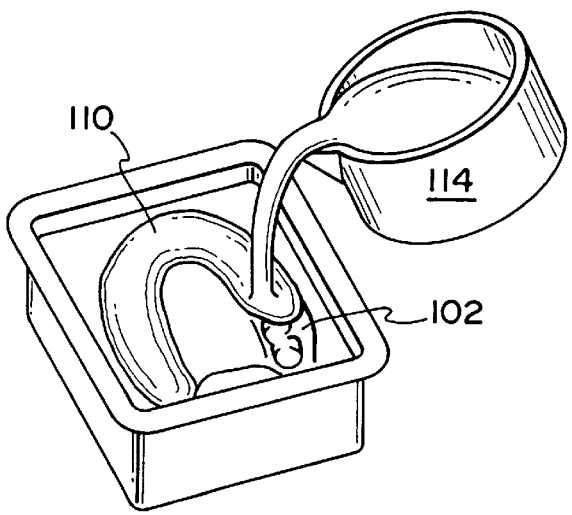
FIG. 14 illustrates the step of pouring a sacrificial material, such as a dental wax or acrylic, into the set hydrocolloid negative of FIG. 13.

FIG. 14 illustrates the step of filling hydrocolloid negative 102 with a sacrificial substance 110, such as a base plate dental wax. As illustrated, hydrocolloid negative 102 of the lower denture has almost been completely filled with sacrificial substance 110. Good results have been achieved when a container 114 filled with sacrificial material 110 is used to dispense sacrificial material 110 in the form of a melted dental wax. For simplicity, and to enhance heat conductivity to assist in the melting of wax 110, container 114 may be made of metal such as stainless steel.

Good results have been achieved when a stainless steel container 114 having a volume equal to about the volume of a standard American coffee cup has been used in conjunction with a standard coffee cup or beverage heater for use on one's office desk.

One should ensure that any hydrocolloid 70 which may have flowed onto the jaw side of denture 40 has been removed.

After hydrocolloid negative 102 has been completely filled, the assistant then fills regions of the dental stone negative 92 of the jaw side of denture 40 with wax 110 which regions might be difficult to fill simply by aligning and pressing together dental stone negative 92 with hydrocolloid negative 102. For example, an eye dropper 122 has been successfully used to dispense controlled amounts of wax 110 into narrow, deep regions of dental stone negative 92. When using an eye dropper 122, a glass eye dropper 122 may be used. In that manner, the glass portion of eye dropper 122 other than the typical rubber bulb 126 may be preheated prior to drawing up wax 110 into eye dropper 122. In that manner, wax 110 remains liquid for a longer period of time. Preheating may be accomplished by use of a traditional bunsen burner or a hand-held butane burner, as such are readily available.

Figure 12:
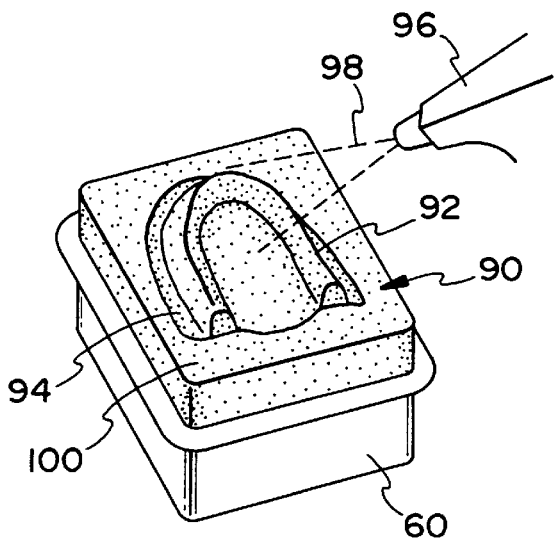
FIG. 12 shows the inventive step of lubricating the hardened dental stone in the inverted top of the inventive box after the dental stone poured in the step of FIG. 11 has hardened, and after the bottom and top halves of the box have been separated, with the dental stone negative of the jaw side of the existing denture visible after the existing denture has been separated from the hardened dental stone.

Examples of narrow and/or deep regions of dental stone negative 92 which may be filled with wax 110 from eyedropper 122 include grooves 94 discussed above in connection with FIG. 12.

Preferably, wax 110 which flows outside of the region of dental stone negative 92 should be wiped off. By removing such excess wax from the land portion 100 of the hardened dental stone 90 mold, such excess wax 110 will not harden on land portions 100. By keeping land portion 100 free of excess wax 110, one is ensured of more accurate mating of the two halves of the negative molds; i.e., the removal of excess wax 110 from land portions 100 will help ensure that dental stone negative 92 of the jaw side of denture 40 and hydrocolloid negative 102 of the lingual side of denture 40 may be brought together without interference from wax build up on the land portions. Such build up can lead to an undesired shifting of hydrocolloid negative 102 away from dental stone negative 92 so that the overall resultant sacrificial material positive 130 (FIG. 19) is inaccurate. For example, in the case where wax 110 is used to make sacrificial material positive 130 the bite of the wax positive 130 of the denture will be increased by an amount substantially equal to the amount of wax build up between the two halves of the mold owing to the two halves of the mold being forced apart (i.e., owing to the two halves of the mold being prevented from correctly seating against other).

Figures 15, 16:
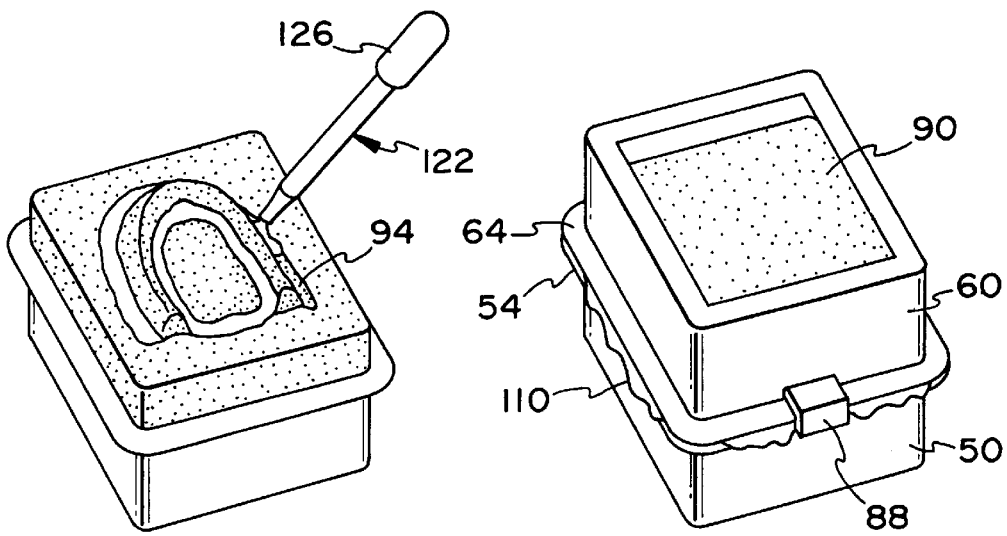
FIG. 15 illustrates the filling of at least portions of the set dental stone negative of the jaw side of the existing denture shown in FIG. 12 with a sacrificial material such as a dental wax or acrylic.
FIG. 16 illustrates the pressing together of the top and bottom halves of the inventive box after the filling of the respective negative molds of the existing denture shown in FIGS. 14 and 15.

FIG. 16 shows the re-pressing together and clamping of the two halves of the sacrificial material-filled mold together; e.g., the pressing together of the wax-filled dental stone negative 92 disposed in upper box 60 against the wax-filled hydrocolloid negative 102 disposed in the hydrocolloid-filled bottom box 50.

Preferably, one has filled respective dental stone negative 92 and hydrocolloid negative 102 with sufficient excess sacrificial material, such as wax 110, so that wax 110 flows out between respective mating flanges 64 and 54 of the upper and lower boxes 60 and 50. Such squeezed out wax 110 serves as a visual confirmation that sufficient wax 110 had been used to fill both halves of the negative mold, and that sufficient force had been applied to press liquid wax 110 into the various void regions of the respective negatives.

The result is a sacrificial material positive 130 of the existing denture 40, which positive 130 may be conveniently made of dental wax 110.

Figures 17, 18:
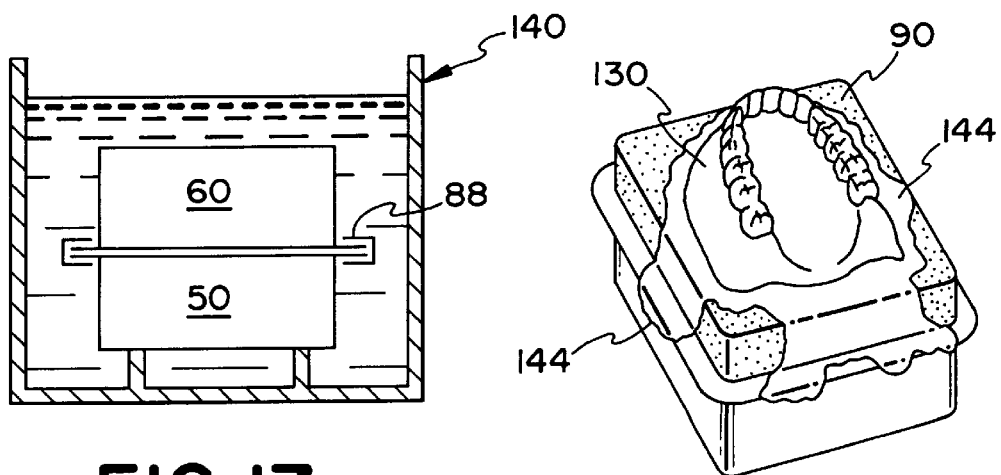
FIG. 17 illustrates the use of a fluid bath to speed up the hardening of the sacrificial material in the step of FIG. 16.
FIG. 18 illustrates the removed top half of the inventive box revealing the hardened complete pattern or sacrificial positive of the existing denture.

FIG. 17 illustrates the placement of the clamped mold has into a water bath 140 to speed up the entire solidification process of sacrificial material positive 130.

After the wax positive has sufficiently cooled, upper box 60 is separated from bottom box 50 to reveal the hardened sacrificial material positive 130 of FIG. 18.

FIG. 18 illustrates such sacrificial material positive 130 seated on dental stone 90. That is, the wax positive of the denture is seated in dental stone negative 92, as the tooth and gum regions of the sacrificial material positive has been withdrawn from hydrocolloid negative 102.

The assistant then removes a wax flange 144 which typically is formed between the two halves of the mold when the two halves are pressed together in the step of forming the sacrificial material positive 130.

Good results have been achieved when the bulk of wax flange 144 is removed from the desired portions of the wax positive by cutting away portions of the wax flange from the wax positive 130 while the wax positive is seated on the dental stone 90. Such cutting away of the wax flange can be accomplished by using a knife and cutting through wax 110 while pressing the knife against dental stone 90 substantially adjacent to the desired portion of wax positive 130. After the bulk of wax flange 144 have been removed from the wax positive while the positive is seated in the mold, the wax positive 130 may be removed, and the final trimming away of the undesired portions of the wax flange 144 may be carried out.

Figure 19:
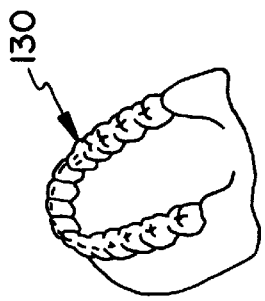
FIG. 19 illustrates the complete pattern or sacrificial positive formed in step 18 after removal of excess sacrificial material, such as flanges.

FIG. 19 illustrates the resultant wax positive or sacrificial material positive 130 of the upper denture.

Preferably, the resultant wax positive 130 is cleaned, chilled in water, and placed in the patient's mouth for a final fitting by the dentist before shipping the wax positive off to a lab, for example, for conversion into a denture.

As required, a wax positive 150 of a complete (or partial) lower denture may be made in a manner similar to the making of the wax positive 130 of the upper denture described above.

Figure 20:
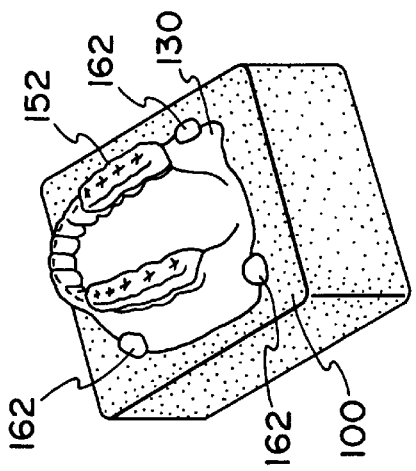
FIG. 20 illustrates the step of using a corrective sacrificial material, such as corrective dental wax, to correct the patient's "bite" in conjunction with the complete sacrificial material positive of the upper and lower old dentures.

FIG. 20 schematically illustrates the wax positive 130 and 150 of upper and lower denture, respectively, placed in a patient's mouth for fitting. As illustrated, an undesirable space between the teeth of the wax positive of the upper denture and the front teeth of the wax positive of the lower denture has been filled with a corrective inner occlusal record material 152, such as a corrective wax, such as Aluwax. By softening the corrective wax, as required, and then having the patient bite down gently on the upper and lower wax positive of the dentures, the dentist is given an accurate view of the correct location and manner at which to fuse such corrective wax 152 to the upper denture wax positive 130, as illustrated. Typically, at least the denture opposing the denture to be corrected (i.e., the denture without corrective wax 152 thereon) is chilled as required. A separating medium (e.g., saliva, water, or petroleum jelly) is applied to the occlusal surface opposite to the one on which the corrective wax is disposed. The patient then bites down with the chilled denture onto the corrective wax or onto the natural teeth. The corrective wax 152 is formed in the desired manner owing to the pressing thereon by the patient. The dentist makes final changes to corrective wax 152, as necessary.

Figure 21:
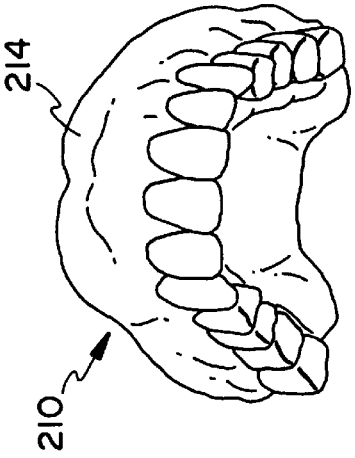
FIG. 21 shows the complete sacrificial material positive of corrected lower denture reseated on its stone mold and adhered thereto for shipment to an off-site laboratory.

As shown in FIG. 21 the corrected denture(s) are put back onto the respective hardened dental stone casts 90 for further treatment or for shipment. The hardened hydrocolloid material negatives may be discarded.

It is contemplated that some dentist will want to form plaster or dental stone models of the dentures by pouring plaster into the hydrocolloid mold negatives prior to discarding such, although such plaster copies need not generally be made.

In the case where the wax positive 130 of the dentures are to be shipped to an off-site laboratory for conversion into a finished new denture, the upper wax positive 130 are placed onto their respective dental stone negatives 92, as shown in FIG. 21. Wax positive 130 is seated correctly, and then an amount of a wax 162 is adhered to both wax positive 130 and dental stone 90.

Preferably, a sufficient amount of securing wax 162 is provided, and at different locations along the interface between land portion 100 of dental stone 90 and wax positive 130 so that the thus secured wax positive and dental stone 90 can be shipped by common carrier to the off-site laboratory without being dislodged from the cast.

Good results have been achieved when the hardened hydrocolloid is removed from the respective mating bottom box 50, and the empty bottom boxes 50 are then mated with the paired top boxes 60 containing the dental stone negative 92 and the wax or sacrificial material positive 130. The top and bottom boxes can then be secured together for shipment by use of a rubber band or other securing means. It is believed that the insulating layer of the air in the void of the empty bottom box 50, as well as the high specific heat of the dental stone 90 prevent wax positive 130 from overheating and melting during shipment on a common carrier even under high temperature conditions.

Figure 22:
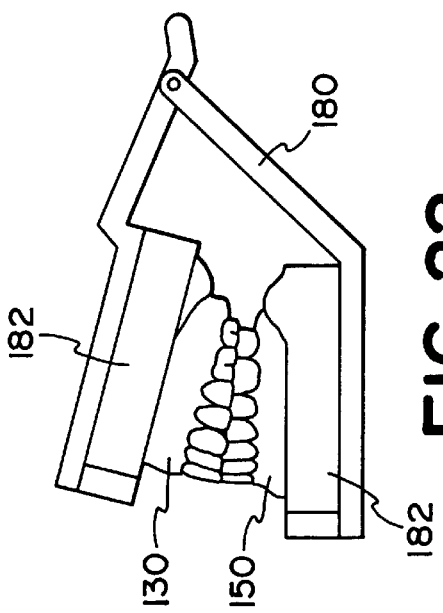
FIG. 22 illustrates the inventive step of complete upper and lower sacrificial material dentures mounted on respective dental stone bases, and each of which are mounted on an articulator for manipulation in the laboratory.

FIG. 22 illustrates the mounting of wax positive 130 and wax positive 150 on their respective dental stones 90 and in turn mounted on an articulator 180. Typically, the lab technician will shape each respective base portion 182 of dental stone 190 in a conventional manner for securing to articulator 180. Such shaping of dental stone 90 includes grinding away portions of base 182, as well as removing regions of land portion 100 of dental stone 90, as required for mounting.

In the case where an off-site laboratory is used, thanks to the present invention method the lab technical may mount the dental stone 90 and wax positive 130 and 150 onto articulator 180, unlike in the prior art method where office personnel, such as dental assistants, attempted the specialized task of mounting onto articulator 180. The lab technician establishes the proper vertical and centric positions of the wax positive.

Thanks to the provision of wax positive copies of the patient's teeth 188, the laboratory technician is provided with precise physical and visual data as to the required size, position, and vertical and centric disposition of the patient's teeth as such are to be provided in prosthetic form in the resultant denture.

Typically, the dentist will write a prescription for at least features of a color/shade of a prosthetic tooth 202, as well as the color/shade of a acrylic or plastic gum portion 214 for use by the laboratory technician.

Preferably, the laboratory technician uses the wax tooth positive 188 to select one of hundreds of standard pre-cast prosthetic teeth 202. Namely, the laboratory technician will typically have available a variety of prosthetic teeth of various types, sizes, and shades, from which the technician will select the correct prosthetic tooth 202 of FIG. 23 that the technician substitutes for the wax tooth positive 188 based on the dentist's instructions.

As a result, a plurality of individual synthetic teeth of the proper size, shape, color, and position may be disposed directly in a wax gum portion 206. After all individual prosthetic teeth 202 are position in wax buccal flange or gum portion 206, the final processing of the denture may be carried out in a standard fashion by known acrylic processing methods to result in the complete new denture 210 having acrylic or plastic gum portion 214 in which individual prosthetic teeth 202 are embedded.

The substitution of the acrylic or other synthetic material 214 for wax gum portion 206 may be carried out by a standard lost wax casting process.

Figure 23:
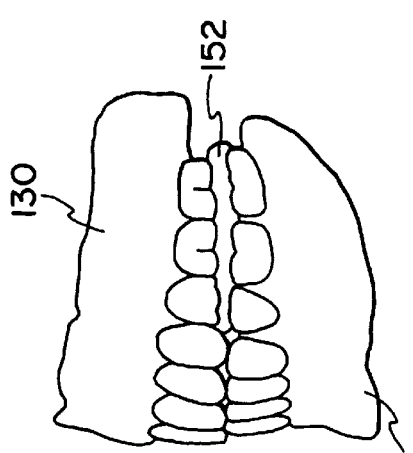
FIG. 23 illustrates the new dentures prior to casting, in which individual pre-cast prosthetic teeth are being/have been substituted for the sacrificial material teeth which guide the lab technician in the selection and placement of such pre-cast prosthetic teeth.
Figure 24:
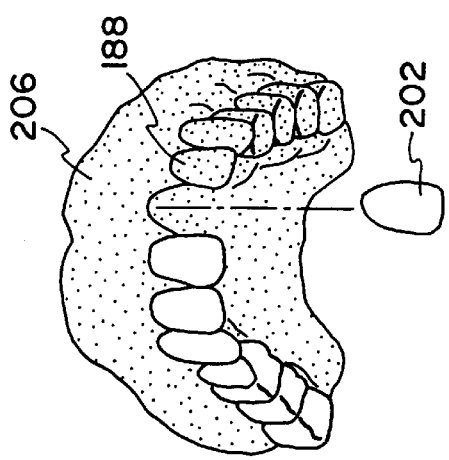
FIG. 24 illustrates the complete new denture according to the invention, in which an acrylic has replaced the gum portion of the sacrificial material thereby forming the complete denture.

It is likewise contemplated that a dentist may for some particular reason wish to have the partially completed denture of FIG. 23 with wax gum portion 206 and prosthetic teeth 202 therein returned for a final fitting prior to the step of substituting acrylic portion 214 for wax gum portion 206.

This inventive aspect of substituting individual prosthetic teeth 202 for wax positive teeth 188 avoids the conventional fluid pour resin methods which have been known in the past to cause allergic reactions.

The above described method works equally well for patient's having partial dentures or only upper dentures, for example. In the case where the patient has solely upper dentures, for example, the dentist may still make a wax copy of the existing natural teeth for use by lab technicians as a reference against which the technicians compare the fit of the new upper denture being made. The wax copy of such natural lower teeth is also useful because patient's natural teeth are almost never contained in a common plane, unlike typical dentures nowadays.

It will be appreciated that all the above objects of the invention have been achieved, as well as advances not specifically enumerated as objects of the invention.

Properly fitting dentures eliminate the use of denture adhesives, which use is discouraged under current theories.

Accurate physical records (i.e., required patient data regarding the vertical positioning, the bite, the position of the teeth, the size of the teeth, and the like) have been achieved by the provision of the accurate (corrected, as needed) wax copy/positive of the patient's dentures and/or natural teeth. Such a physical, 3-dimensional model is easier for a technician to use than prior art written records, and results in fewer errors in transcription and understanding than was the case with prior art written dental prescriptions.

If the dentist does not like the position of wax copy/positive of the teeth, for example, then he or she can easily heat up the wax positive and reposition and/or shorten one or more of the wax positive teeth.

Fewer lab technicians are required, higher accuracy in reproduction and production of synthetic dental prostheses such as dentures is achieved, and the need to make written specifications for at least positioning, if not all reproduction is illuminated.

It has been found that patient's outfitted with dentures made according to the inventive technique adapt to the new dentures in less than half the time required for adapting to the dentures made by prior art methods. Likewise, fewer than half the number of adjustments of the inventive dentures is required as compared with prior art dentures. Good results have been achieved by outfitting patient's in 1 or 2 return visits to the dentist's office as opposed to the often 6 to 8 office visits required when using past techniques of fabricating dentures.

Such improvements likewise save money and time for the patient as well as the dentist owing to fewer return visits and "chair time" with the dentist, respectively.

It is contemplated that alignment marks or key will be provided on the upper and lower boxes to ensure that the two are properly seated. It is further contemplated that boxes of shapes other than square/rectangles be used to ensure correct positioning of the upper and lower boxes when clamping together.

A slurry water may be used as a catalyst in the step of casting with dental stone. Lab plaster may be substituted for dental stone.

A reversible hydrocolloid may be used instead of an irreversible hydrocolloid.

Corrective wax may be a standard brand such as "Aluwax."

While this invention has been described as having a preferred design, it is understood that it is capable of further modifications, and uses and/or adaptions of the invention and following in general the principle of the invention and including such departures from the present disclosures as come within the known or customary practice in the art to which the invention pertains, and as may be applied to the central features hereinbefore set forth, and fall within the scope of the invention or limits of the claims appended hereto.

What is claimed is:

1. A method of making a new dental prosthesis from an existing dental prosthesis, comprising:
   a) making a sacrificial positive of the existing dental prosthesis;
   b) using the sacrificial positive of the existing dental prosthesis to form a new dental prosthetic; and
   c) using the sacrificial positive of the existing dental prosthesis as a guide to placement of a new prosthetic tooth.

2. A method as in claim 1, wherein:
   a) the step of making a sacrificial positive of the dental prosthesis includes making a sacrificial positive of a part of an existing denture.

3. A method as in claim 2, wherein:
   a) the step of making a sacrificial positive of a part of an existing denture includes making a sacrificial positive of a tooth disposed in a sacrificial gum portion.

4. A method as in claim 2, further comprising the step of:
   a) making a prosthetic denture.

5. A method as in claim 1, wherein:
   a) the step of making a sacrificial positive of the existing dental prothesis includes making a negative of the existing dental prosthesis in a first material.

6. A method as in claim 1, wherein:
   a) the step of making a sacrificial positive of the existing dental prosthesis includes making a negative of a first portion of the existing dental prosthesis in a first material and a negative of a second portion of the existing dental prosthesis in a second material.

7. A method as in claim 6, wherein:
   a) a substantially complete sacrificial positive of an existing dental prosthesis is made by using the negative of the first portion in the first material and the negative of the second portion in the second material to cast the substantially complete sacrificial positive of the dental prosthesis.

8. A method as in claim 7, wherein:
   a) the first material is softer than the material of the sacrificial positive; and
   b) the second material is harder than the material of the sacrificial positive.

9. A method as in claim 7, wherein:
   a) the first material is a hydrocolloid; and
   b) the second material is a castable stone.

10. A method as in claim 6, wherein:
    a) in said step of making a negative of a first portion of a sacrificial positive of the existing dental prosthesis, the existing dental prosthesis is placed in non-set first material, the first material is allowed to set, and a portion of the set first material substantially adjacent to the existing dental prosthesis placed in the first material is removed prior to removing the existing dental prosthesis from the set first material.

11. A method as in claim 10, wherein:
    a) a sufficient amount of set first material is removed adjacent the existing dental prosthesis so that the existing dental prothesis can be substantially freely removed from the second material when the second material is placed around the dental prosthesis for forming the negative for the second portion of the existing dental prosthesis.

12. A method as in claim 1, wherein:
    a) the sacrificial positive of the existing prosthesis used as a guide to placement includes a sacrificial positive of a tooth of the existing dental prosthesis.

13. A method as in claim 12, wherein:
    a) in said step of using the sacrificial positive as a guide to placement, a sacrificial tooth is used as a guide for placement of the prosthetic tooth.

14. A method as in claim 13, wherein:
    a) in said step of using the sacrificial positive as a guide to placement, a single sacrificial tooth is removed and replaced by a single prosthetic tooth.

15. A method of making a new dental prosthesis from an existing dental prosthesis, comprising:
    a) making a sacrificial positive of the existing dental prosthesis;

b) modifying the sacrificial positive of the existing dental prosthesis to form a corrected sacrificial positive of the dental prosthesis; and
c) using the corrected sacrificial positive of the existing dental prosthesis to form a new dental prothesis.

16. A method as in claim 15, wherein:
a) the step of making a sacrificial positive of the dental prosthesis includes making a sacrificial positive of a part of an existing denture.

17. A method as in claim 16, wherein:
a) the step of making a sacrificial positive of an existing denture includes making a sacrificial positive of a tooth disposed in a sacrificial gum portion.

18. A method as in claim 17, wherein:
a) in said step of using the corrected sacrificial positive of the existing dental prosthesis to form a new dental prosthesis, the tooth disposed in the sacrificial gum portion is removed and used as a guide for placement of a prosthetic tooth substituted for the removed tooth.

19. A method as in claim 18, wherein:
a) in said step of replacing the sacrificial positive of the tooth with the prosthetic tooth, a single sacrificial tooth is removed and replaced by a single prosthetic tooth.

20. A method as in claim 16, wherein:
a) the dental prosthesis is a denture.

21. A method as in claim 15, wherein:
a) the step of making the sacrificial positive of an existing denture is performed by casting substantially the entire sacrificial positive of a first negative of a part of the existing dental prosthesis made of a first material and a second negative of a second part of the existing dental prosthesis made of a second material.

22. A method as in claim 15, wherein:
a) said steps of making a sacrificial positive of the existing dental prosthesis and said step of modifying the sacrificial positive to form the corrected sacrificial positive of the dental prosthesis are both carried out in a dental practitioner's office.

23. A method as in claim 22, wherein:
a) the corrected sacrificial positive of the dental prosthesis is made during a single visit to the dental practitioner's office.

24. A method as in claim 15, wherein:
a) said step of making the sacrificial positive of the existing dental prosthesis includes:
   i) making a negative of a first side of the existing dental prosthesis in a first material;
   ii) making a negative of a second side of the existing dental prosthesis in a second material;
   iii) using the first material negative and the second material negative as a mold to form the sacrificial positive of the existing dental prosthesis.

25. A method as in claim 24, wherein:
a) said step of making the sacrificial positive of the existing dental prosthesis includes modifying the second side of the existing dental prosthesis prior to the forming of the sacrificial positive of the existing dental prosthesis.

26. A method as in claim 25, wherein:
a) said step of modifying the sacrificial positive of the existing dental prosthesis to form a corrected sacrificial positive of the dental prosthesis includes placing the sacrificial positive of the existing dental prosthesis in a patient's mouth and correcting the sacrificial positive of the existing dental prosthesis.

27. A method as in claim 26, wherein:
a) said step of modifying the sacrificial positive of the existing dental prosthesis includes adding additional sacrificial material to the sacrificial positive prior to placing the sacrificial positive in the patient's mouth, so that when the patient uses the sacrificial positive in the manner that the dental prosthesis would be used, the additional sacrificial material is conformed by the patient's mouth during such use.

28. A method as in claim 24, wherein:
a) the first material includes a hydrocolloid and the second material includes a dental stone.

29. A method as in claim 11, further comprising the step of:
a) making a prosthetic denture.

30. A method of making a new dental prosthesis from an existing dental prosthesis, comprising:
a) making a sacrificial positive of the existing dental prosthesis;
b) using the sacrificial positive of the existing dental prosthesis to form a new dental prosthesis;
c) the step of making a sacrificial positive of the existing dental prosthesis includes making a negative mold of a part of the existing dental prosthesis;
d) a first negative mold of a first part of the existing dental prosthesis is made in a material softer than the existing dental prosthesis;
e) a second negative mold of a second part of the existing dental prosthesis is made in a material harder than the existing dental prosthesis; and
f) the first and second negative molds are used to make a modified substantially entire sacrificial positive of the existing dental prosthesis.

31. A method as in claim 30, wherein:
a) the substantially entire sacrificial positive of the existing dental prosthesis is modified to change copied elements of the existing denture.

32. A method as in claim 30, wherein:
a) the substantially entire sacrificial positive of the existing dental prosthesis includes a base and at least one tooth.

33. A method as in claim 32, further comprising the step of:
a) using the at least one sacrificial tooth as a guide to placement of a prosthetic tooth.

34. A method as in claim 21, further comprising the step of:
a) making a prosthetic denture.

35. A method as in claim 15, further comprising the step of:
a) making a prosthetic denture.

36. A method as defined in claim 30, wherein:
a) the second part of the existing denture is removed from the second negative mold made of a material harder than the existing denture substantially without the existing denture having been captured by the second negative mold.

37. A method as defined in claim 30, wherein:
a) said steps of making a sacrificial positive of the existing dental prosthesis and using the sacrificial positive of the existing dental prosthesis to form a new denture are carried out substantially without harming the existing denture.

* * * * *